US00PP24643P3

(12) United States Plant Patent
Schäfer

(10) Patent No.: US PP24,643 P3
(45) Date of Patent: Jul. 15, 2014

(54) VARIETY OF BASIL PLANT NAMED 'HABANA'

(50) Latin Name: *Ocimum basilicum*
Varietal Denomination: Habana

(75) Inventor: Udo Schäfer, Wolsier (DE)

(73) Assignee: Herbalea GmbH, Grolsheim (DE)

( * ) Notice: Subject to any disclaimer, the term of this patent is extended or adjusted under 35 U.S.C. 154(b) by 122 days.

(21) Appl. No.: 13/385,806

(22) Filed: Mar. 7, 2012

(65) Prior Publication Data

US 2013/0239272 P1 Sep. 12, 2013

(51) Int. Cl.
*A01H 5/00* (2006.01)
*A01H 5/02* (2006.01)

(52) U.S. Cl.
CPC ..... *A01H 5/02* (2013.01)
USPC ..... Plt./258

(58) Field of Classification Search
CPC ..... A01G 31/06; C07C 67/08
USPC ..... Plt./258
See application file for complete search history.

(56) References Cited

U.S. PATENT DOCUMENTS

PP13,486 P2 * 1/2003 Bowden et al. ..... Plt./258
PP16,260 P2 * 2/2006 Bennerup ..... Plt./258

OTHER PUBLICATIONS

QZ PBR Application Publication for 'Habana' Feb. 15, 2011.*

* cited by examiner

*Primary Examiner* — Wendy C Haas
(74) *Attorney, Agent, or Firm* — The Webb Law Firm

(57) ABSTRACT

'Habana' is a new variety of basil plant having a tall growth habit, high leaf count, and tolerance to low temperatures.

4 Drawing Sheets

Botanical classification: *Ocimum basilicum.*
Variety denomination: 'HABANA'.

CROSS REFERENCE TO RELATED APPLICATIONS

The new variety was discovered in the same cultivated area as basil plants named 'Ajaka', 'Dark Lady', and 'Green Fortune', each respectively claimed in U.S. Plant patent application Ser. Nos. 13/385,808, 13/385,798, and 13/385,811.

BACKGROUND OF THE NEW PLANT

The present invention comprises a new and distinct cultivar of basil plant, botanically known as *Ocimum basilicum* and hereinafter referred to by the cultivar name 'Habana'.

The new variety was discovered and selected by the breeder in a cultivated environment in July of 2009 in Wolsier, Germany (located in the region of Brandenburg) as a naturally occurring open-pollinated new variety in a population of unpatented and unnamed *Ocimum basilicum* plants. Subsequently, the new variety was asexually reproduced by cuttings in Wolsier, Germany in 2010. Further asexual reproductions at the same location has demonstrated that the combination of characteristics as herein disclosed for the new cultivar are retained and reproduced true to type through successive generations of asexual reproduction.

The following observations, measurements and comparisons describe 8-week-old plants grown in an open field with full sun, watered as needed, and receiving weekly fertilization treatments accented with nitrogen in Wolsier, Germany. The plants were exposed to daytime temperatures of 20-30° C., and evening temperatures of 10-20° C. Color observations were taken under natural light, and the color references are made to The R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Habana' which, in combination, distinguish this basil plant as a new and distinct cultivar:

1. Tall and dense plant habit;
2. Rich and pleasant fragrance;
3. Aromatic taste;
4. Tolerant to *Fusarium, Botrytis*, and *Pythium*; and
5. Low temperature tolerance.

Further, the new variety exhibits an aromatic taste like basil variety 'Green Ball' (U.S. Plant patent application Ser. No. 13/385,809). However, 'Habana' has a tall growth habit, while 'Green Ball' has a compact growth habit. The following Table 1 provides a further comparative listing of botanical characteristics of 'Habana' and 'Green Ball'.

TABLE 1

| Botanical characteristics | 'Habana' | 'Green Ball' |
|---|---|---|
| Height from soil to top of plant: | 50 cm. | 20 cm. |
| Leaf length: | 3.5 cm. | 2 cm. |
| Number of leaves per plant: | About 800 | Over 700 |
| Flower production: | Yes | No |

BRIEF DESCRIPTION OF THE DRAWINGS

The accompanying photographic drawings illustrate the new variety, with the colors being as nearly true as is possible with color illustrations of this type.

DESCRIPTION OF THE PLANT

Figure 1:
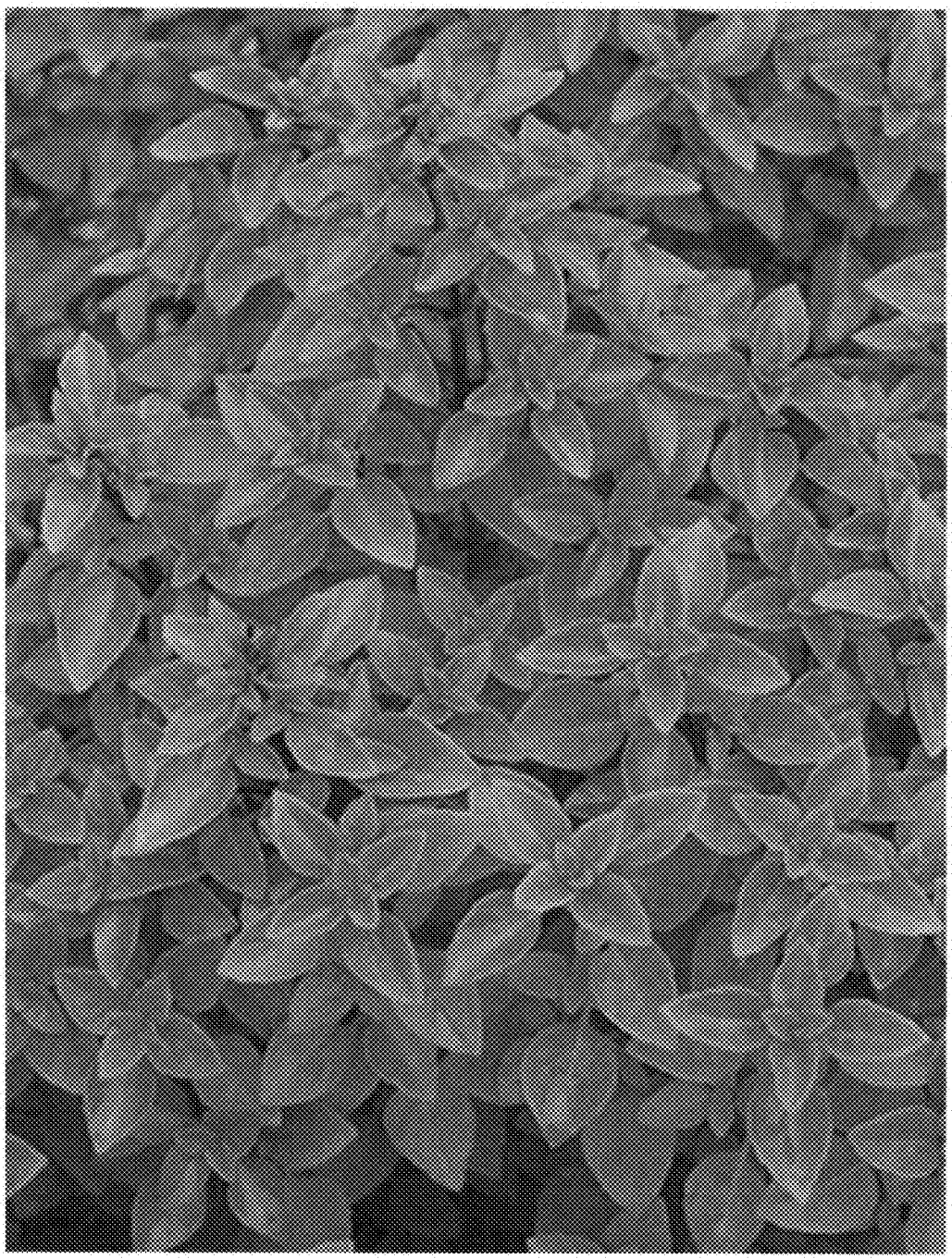
FIG. 1 is a photograph of the leaves of the new variety.
Figure 2:
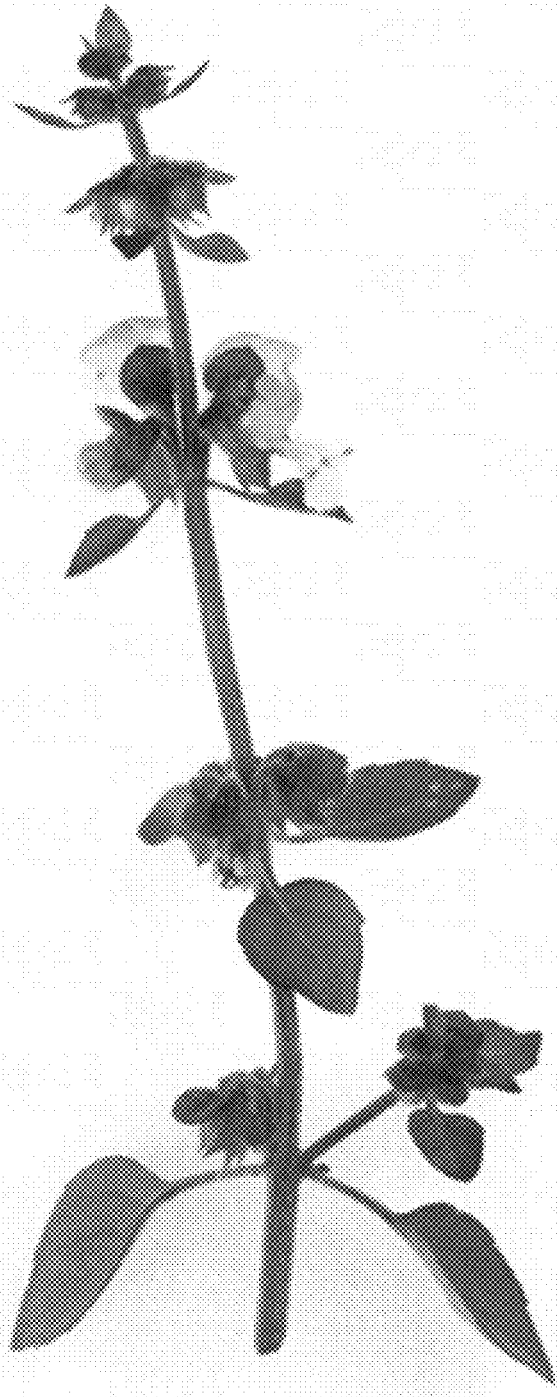
FIG. 2 is a photograph of the flowers of the new variety.
Figure 3:
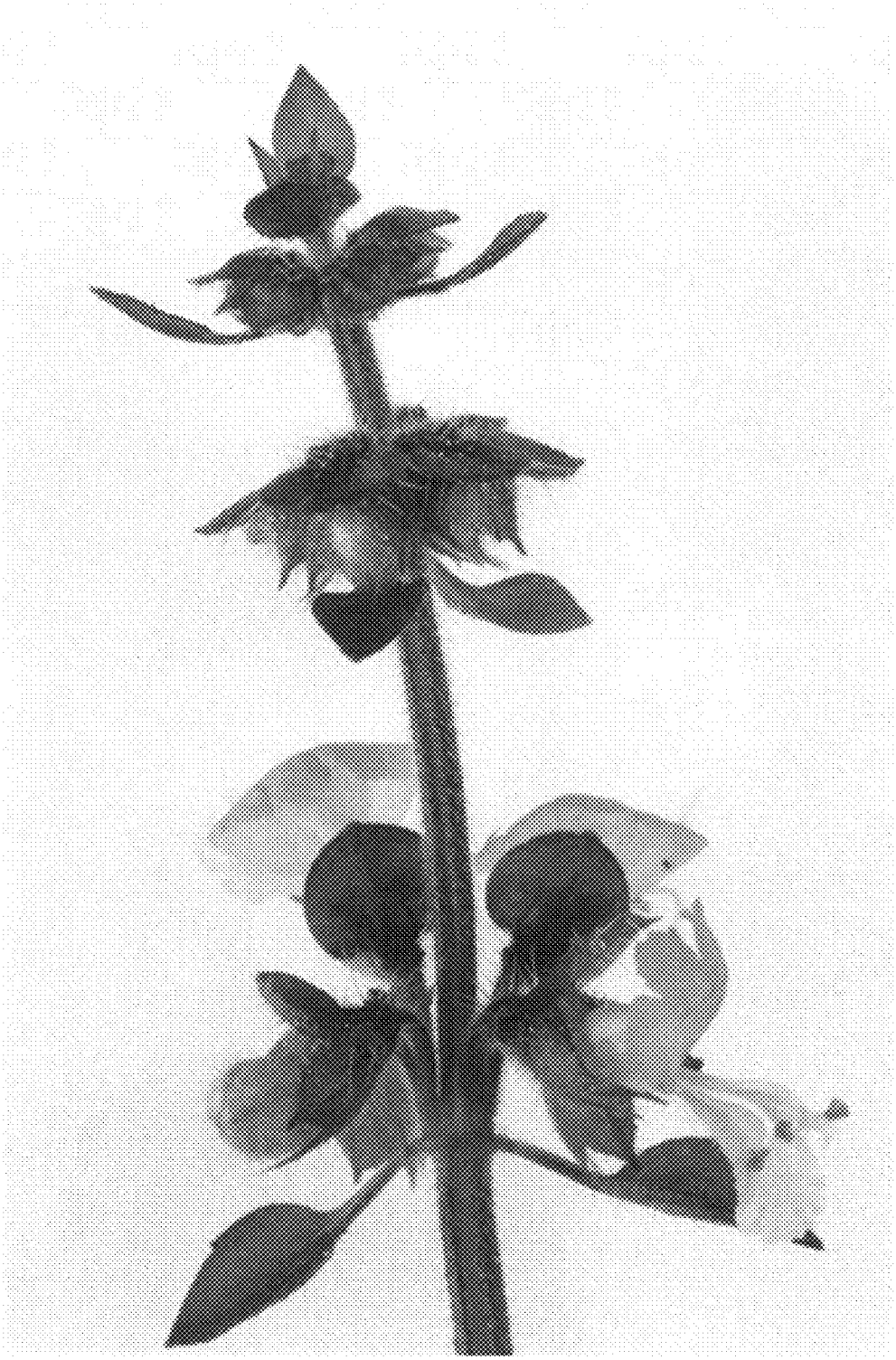
FIG. 3 is a close-up photograph of the flowers of the new variety.
Figure 4:
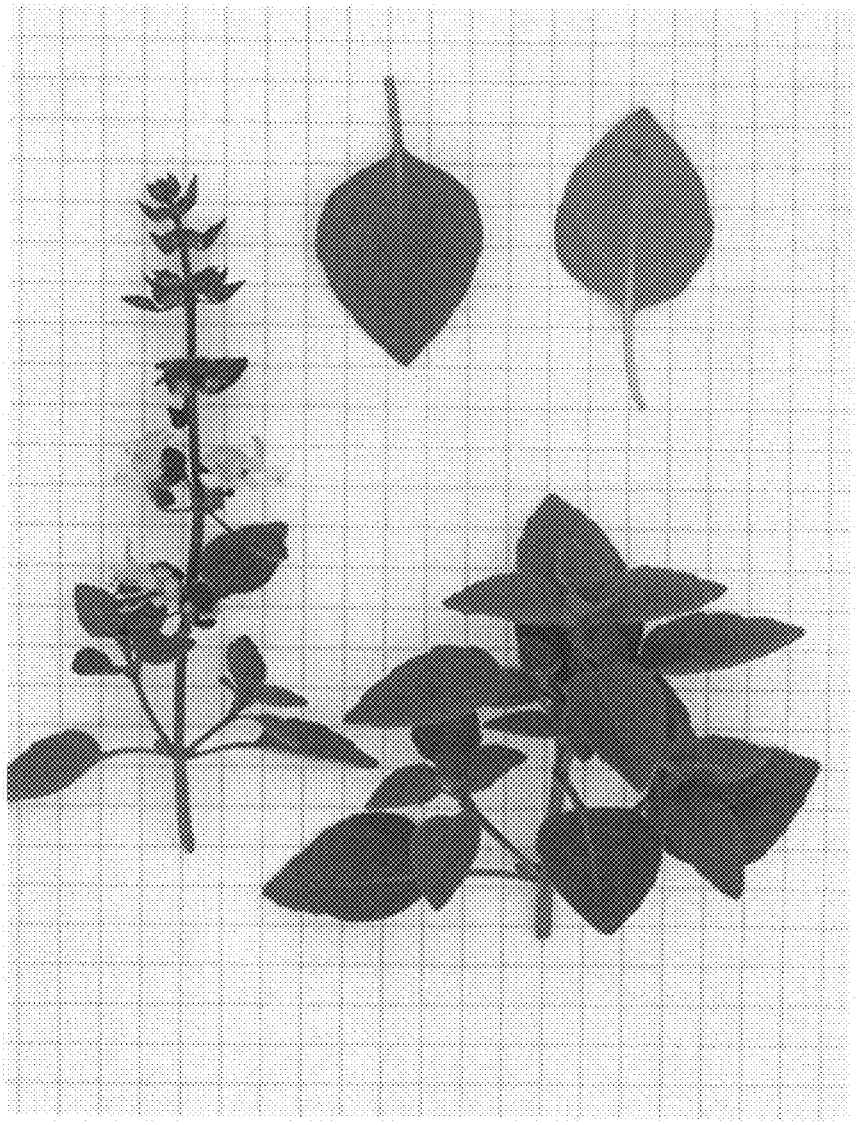
FIG. 4 is a photograph of detached leaves and flowers of the new variety.

Time to initiate roots: 5 days at 22° C.

Time to produce a rooted plant: 9 days at 22° C.

Root description: Finely branched white roots with a fibrous habit.

Form: Erect.

Height from soil to top of plant: 50 cm.

Plant diameter: 50 cm.

Growth habit: Loose with a low-branching habit.

*Vigor*.—Strong, when compared to 'Wild Magic' (U.S. Plant patent application Ser. No. 13/385,805 and 'Green Ball' (U.S. Plant patent application Ser. No. 13/385,809).

Main stem:

*Length*.—50 cm.

*Width*.—0.3 cm.

*Color*.—Yellow-Green Group RHS 145B.

*Number of branches*.—10-20.

*Node spacing*.—1-4 cm.

Leaves:

*Arrangement*.—Decussate; pinnate.

*Number of leaves per plant*.—About 800.

*Length*.—3.5 cm.

*Width*.—2.5 cm.

*Shape of leaf* (*generally*).—Cordate.

*Shape of apex*.—Acute.

*Shape of base*.—Cordate.

*Texture*.—Pubescence is present on the stem and petiole. Small veins are present on the upper surface, with stronger venation on the lower surface.

*Aspect*.—Horizontal.

*Margin type*.—Entire.

*Upper surface color*.—Green Group RHS 137C.

*Lower surface color*.—Green Group RHS 137C.

*Veins*.—Upper surface description and color: Pinnate; Yellow-Green Group RHS 146C. Lower surface description and color: Pinnate; Green Group RHS 139C.

*Petiole*.—Length: 2 cm. Diameter: 1 mm. Color: Green Group RHS 137C. Texture: Scant pubescence present. Shape: Round.

Reproductive organs: 1 pistil and 4 stamens present.

Flowers:

*Natural flowering season*.—End of June through September in the Brandenburg Region of Germany.

*Number of flowers per plant*.—About 50.

*Fragrance*.—Aromatic.

*Longevity*.—4-6 weeks.

*Flower type*.—Labiate.

*Flower height*.—0.5 cm.

*Flower diameter*.—0.3 cm.

*Petal color*.—Upper surface: Purple-Violet Group RHS N80D and White Group RHS999D. Lower surface: Purple-Violet Group RHS N80D and White Group RHS999D.

Seed description: Sterile.

Disease/pest resistance: Resistant to *Fusarium oxysporum* and tolerant to *Botrytis cinerea*.

Weather tolerance: Very tolerant to rain and cold nights (down to 8° C.).

Harvesting season: Early summer to fall outdoors; year round indoors.

Flavor: Flavorsome.

Aroma: Condiment-like.

Essential oils: Eugenol methyl ether-Eugaenol-type.

Productivity/yield per acre:

*Fresh*.—22 tons per acre.

*Dried*.—3 tons per acre.

Average life span: 5 months.

Use: Multiple uses. The new variety can be used as a pot plant, ornamental plant, culinary herb, or fresh and dried herb.

Fresh shelf life: Over 1 week under cool conditions (5-8° C.).

I claim:

1. A new and distinct variety of basil plant named 'Habana' as herein described and illustrated.

* * * * *